United States Patent [19]

Murayama et al.

[11] 3,940,401
[45] Feb. 24, 1976

[54] 4,4-(O-PHENYLENEDIOXY)-2,2,6,6-TETRAMETHYL PIPERIDINE

[75] Inventors: Keisuke Murayama; Toshimasa Toda; Eiko Mori; Katsuaki Matsui; Tomoyuki Kurumada; Noriyuki Onta; Ichiro Watanabe, all of Tokyo, Japan

[73] Assignee: Sankyo Company Limited, Japan

[22] Filed: July 24, 1974

[21] Appl. No.: 491,489

Related U.S. Application Data

[60] Continuation of Ser. No. 336,981, March 1, 1973, abandoned, which is a division of Ser. No. 219,133, Jan. 19, 1972, Pat. No. 3,790,525.

[52] U.S. Cl. ..... 260/293.58; 260/293.66; 260/293.9
[51] Int. Cl.² .................................. C07D 211/44
[58] Field of Search ................ 260/293.66, 293.58

[56] References Cited
FOREIGN PATENTS OR APPLICATIONS
660,763  9/1965  Belgium

OTHER PUBLICATIONS
Chemical Abstracts 61:2364h, (1964), Chodera et al.

Primary Examiner—Sherman D. Winters
Attorney, Agent, or Firm—Toren, McGeady and Stanger

[57]  ABSTRACT

4-Piperidone ketal derivatives of the formulae

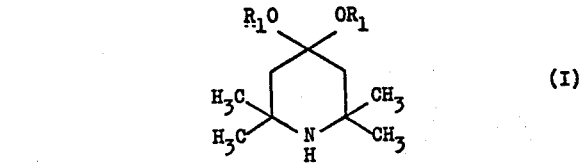

and

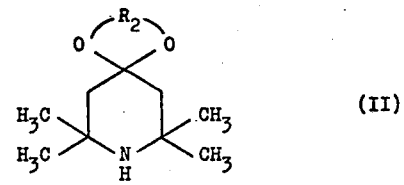

wherein $R_1$ represents an alkyl group of 1 to 8 carbon atoms and $R_2$ represents an alkylene group of 2 or 3 carbon atoms or o-phenylene group and they are prepared by reacting triacetonamine with a monohydric alcohol of the formula $$R_1\text{—OH} \qquad \text{(III)}$$

wherein $R_1$ is as defined above or a dihydric alcohol or phenol of the formula $$R_2\text{—(OH)}_2 \qquad \text{(IV)}$$

wherein $R_2$ is as defined above in the presence of an acid catalyst. They are useful as statilizers against deterioration of synthetic polymers.

1 Claim, No Drawings

4,4-(O-PHENYLENEDIOXY)-2,2,6,6-TETRAMETHYL PIPERIDINE

This is a continuation of application Ser. No. 336,981, filed Mar. 1, 1973, now abandoned, which in turn was a Divisional of application Ser. No. 219,133, filed Jan. 19, 1972, now U.S. Pat. No. 3,790,525.

This invention relates to new 4-piperidone ketal derivatives, their preparation and their use as stabilizers.

More particularly, this invention is concerned with the 4-piperidone ketal derivatives having the formulae

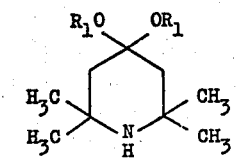

and

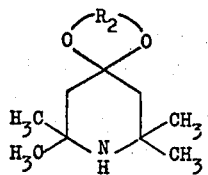

wherein $R_1$ represents an alkyl group of 1 to 8 carbon atoms and $R_2$ represents an alkylene group of 2 or 3 carbon atoms or o-phenylene group, a process for the preparation of the 4-piperidone ketal derivatives (I) and (II) and stabilization of synthetic polymers against photo- and thermal-deterioration thereof by having incorporated therein, in a sufficient amount to prevent said deterioration, at least one of the 4-piperidone ketal derivatives (I) and (II).

In the above formulae (I) and (II), $R_1$ may be illustrated by methyl, ethyl, n-propyl, isopropyl, n-butyl, tert.butyl n-pentyl, isopentyl, hexyl, heptyl and octyl; and $R_2$ may be illustrated by ethylene, trimethylene, propylene and o-phenylene.

The term "synthetic polymer" as used herein are intended to embrace polyolefins including homopolymers of olefins such as low-density and high-density polyethylene, polypropylene, polystyrene, polybutadiene, polyisoprene and the like, and copolymers of olefins with other ethylenically unsaturated monomers such as ethylene-propylene copolymer, ethylene-butene copolymer, ethylene-vinyl acetate copolymer, styrenebutadiene copolymer, acrylonitrile-styrene-butadiene copolymer and the like;

polyvinyl chlorides and polyvinylidene chlorides including homopolymer of each of vinyl chloride and vinylidene chloride, vinyl chloride-vinylidene chloride copolymer and copolymers of each of vinyl chloride and vinylidene chloride with vinyl acetate or other ethylenically unsaturated monomers;

polyacetals such as polyoxymethylene and polyoxyethylene; polyesters such as polyethylene terephthalate; polyamides such as 6-nylon, 6,6-nylon and 6,10-nylon; and polyurethanes.

Synthetic polymers have been widely utilized in the art, in view of their excellent properties, in various forms or shapes, for example, filament, fibre, yarn, film, sheet, other molded article, latex and foam. However, these polymers have some drawbacks such as poor light- and heat-stabilities and the like. Stated illustratively, polyolefins and polyurethane elastomers frequently tend to undergo severe deterioration when exposed to light such as sunlight or ultraviolet ray, and polyvinyl chloride and polyvinylidene chloride frequently tend to deteriorate and become colored by the action of light and heat together with elimination of hydrogen chloride therefrom. Polyamides are also frequently subjected to photo-deterioration. For the purpose of stabilizing these synthetic polymers against such deterioration, there have heretofore been proposed in the art a number of stabilizers; for example, for polyolefins, benzotriazole compounds and benzophenone compounds; for polyurethanes, phenol compounds and benzophenone compounds; and for polyvinyl chloride and polyvinylidine chloride, lead salts such as basic lead silicate and tribasic lead maleate, and organotin compounds such as dibutyltin laurate and dibutyltin maleate.

Although such prior stabilizers are known to be considerably satisfactory, there still remained some problems to be improved.

Thus, numerous attempts have been made in the art to find and develop new and more effective stabilizers.

As a result of our extensive studies, it has now been found that the new 4-piperidone ketal derivatives (I) and (II) of this invention can be satisfactorily prepared and exhibit a high stabilizing effect against photo-and thermal-deterioration of the synthetic polymers.

It is, accordingly, an object of this invention to provide new and useful 4-piperidone ketal derivatives (I) and (II).

Another object is to provide a process for the preparation of the valuable 4-piperidone ketal derivatives (I) and (II).

Still another object is to provide synthetic polymer composition stabilized against the deterioration thereof by having incorporated therein a sufficient amount to prevent the deterioration of at least one of the 4-piperidone ketal derivatives (I) and (II).

Other objects of this invention will become apparent to those skilled in the art from the following description.

In one aspect of this invention, the 4-piperidone ketal derivatives (I) and (II) are all new substances unknown in the art.

Representative of the 4-piperidone ketal derivatives of the above formulae (I) and (II) are as follows:

| Compound No. | Chemical Name |
|---|---|
| 1 | 4,4-diethoxy-2,2,6,6-tetramethylpiperidine. |
| 2 | 4,4-di-n-butoxy-2,2,6,6-tetramethylpiperidine. |
| 3 | 4,4-di-n-octoxy-2,2,6,6-tetramethylpiperidine. |
| 4 | 1,4-dioxa-8-aza-7,7,9,9-tetramethyl-spiro-[4.5]decane. |
| 5 | 1,5-dioxa-9-aza-8,8,10,10-tetramethyl-spiro-[5.5]undecane. |
| 6 | 4,4-(o-phenylenedioxy)-2,2,6,6-tetramethyl-piperidine. |

In another aspect of this invention, the 4-piperidone ketal derivatives (I) and (II) of this invention can be easily prepared according to the process of this invention, the process of which comprises reacting 2,2,6,6-tetramethyl-4-piperidone (frequently and hereinbelow referred to as triacetonamine) with a monohydric alcohol having the formula $$R_1 - OH \quad \quad (III)$$

wherein $R_1$ is as defined above or a dihydric alcohol or phenol having the formula $$R_2 - (OH)_2 \quad \quad (IV)$$

wherein $R_2$ is as defined above in the presence of an acid catalyst.

In carrying out the process of this invention, the reaction can be suitably effected by intimately contacting triacetonamine with the monohydric alcohol (III) or the dihydric alcohol (IV) in the presence of the acid catalyst and, advantageously, under reflux in the presence of a suitable organic solvent. As the solvent may be advantageously employed any of inert water-immiscible organic solvents that could not adversely affect the reaction, reactants and catalyst. Examples of the solvent include aliphatic and aromatic hydrocarbons, e.g., n-hexane, cyclohexane, benzene, toluene and xylene.

The monohydric alcohol of the above formula (III) which may be employed in the reaction includes straight or branched monohydric alcohols, e.g., methanol, ethanol, isopropanol and octanol. The dihydric alcohol or phenol of the above formula (IV) which may be employed in the reaction includes, e.g., ethylene glycol, propylene glycol, trimethylene glycol and catechol. The acid catalyst which may be employed in the reaction is any of those catalysts commonly utilized in a standard condensation reaction with elimination of water and includes mineral acids, e.g., hydrochloric acid and polyphosphoric acid; and organic acids, e.g., methanesulfonic acid, benzensulfonic acid and p-toluenesulfonic acid, the organic acids being preferable.

As it is noted that the reaction of the present process be a condensation reaction accompanied with elimination of water, the reaction may be more smoothly and preferably effected with continuous removal of the water that is being formed in situ during the reaction proceeding.

After completion of the reaction, the desired product may be readily recovered and purified in a conventional manner, for instance, by making the reaction mixture alkalihe with an alkali hydroxide, separating an organic layer followed by distillation under reduced pressure and, if necessary, recrystallization.

In still another aspect of this invention, there is provided a synthetic polymer composition stabilized against photo-and thermal-deterioration which contains at least one of the new 4-piperidone ketal derivatives (I) and (II) having incorporated therein.

The 4-piperidone ketal derivatives (I) and (II) employed as a stabilizer in the present invention may be readily incorporated into the synthetic polymers by any of the various standard procedures commonly utilized in the art. The stabilizer may be incorporated into the synthetic polymers at any desired stage prior to the manufacture of shaped articles therefrom. Thus, for example, the stabilizer in the form of a dry powder may be admixed with the synthetic polymer, or a suspension or emulstion of the stabilizer may be admixed with a solution, suspension or emulsion of the synthetic polymer.

The amount of the 4-piperidone ketal derivatives (I) and (II) employed in the synthetic polymer in accordance with the present invention may be varied widely, depending upon the types, properties and particular uses of the synthetic polymer to be stabilized. In general, the 4-piperidone ketal derivatives of the formula (I) and (II) may be added in an amount ranging from 0.01 to 5.0 percent by weight, based on the amount of the synthetic polymer, but the practical range is varied depending upon the type of the synthetic polymer, that is 0.01 to 2.0 percent by weight, preferably 0.02 to 1.0 percent by weight for polyolefins, 0.01 to 1.0 percent by weight, preferably 0.02 to 0.5 percent by weight for polyvinyl chloride and polyvinylidene chloride, and 0.01 to 5.0 percent by weight, preferably 0.02 to 2.0 percent by weight for polyurethanes and polyamides.

The present stabilizer may be used alone or in combination with other known antioxidants, ultraviolet absorbents, fillers, pigments and the like.

If desired, two or more of the present stabilizers i.e. the 4-piperidone ketal derivatives of the formulae (I) and (II) may also be satisfactorily used in this invention.

In order that the invention may be better understood, the following Examples are given solely for the purpose of illustration of this invention. In the Examples, all parts are given by weight unless otherwise indicated and the number of the test compound as used hereinbelow is the same as illustratively shown above.

Examples 1 through 4 describe the preparation of the 4-piperidone ketal derivatives.

Examples 5 through 9 describe the synthetic polymer compositions having incorporated therein the 4-piperidone ketal derivatives and their stablilization effects.

EXAMPLE 1

4,4-Di-n-butoxy-2,2,6,6-tetramethylpiperidine

In a solution of 23.4 g. of triacetonamine in 150 ml. of benzene were added 23.2 g. of n-butanol and 30 g. of p-toluenesulfonic acid. The resulting mixture was heated under reflux for 44 hours by means of a water separator.

Then, the reaction mixture was poured into a cold aqueous solution of sodium hydroxide and the benzene layer was separated therefrom. The layer so separated was washed with water, dried over anhydrous sodium sulfate and subjected to distillation under reduced pressure to give the desired product as colorless liquids boiling at 123°–124°C/4 mmHg.

IR (liquid film) $\nu_{C-O-C}$ 1093, 1037 cm$^{-1}$. Analysis for $C_{17}H_{35}NO_2$: Calculated: C, 71.52%; H, 12.36%; N, 4.91%. Found: C, 71.35%; H, 12.44%; N, 5.14%.

EXAMPLE 2

4,4-Di-n-octoxy-2,2,6,6-tetramethylpiperidine

The substantially same procedure as shown in the above Example 1 was repeated except that n-octanol was employed instead of the n-butanol, thereby yielding the desired product as colorless liquids boiling at 160°–162°C/0.45 mmHg.

IR (liquid film) $\nu_{C-O-C}$ 1092, 1038 cm$^{-1}$. Analysis for $C_{25}H_{51}NO_2$: Calculated: C, 78.67%; H, 13.47%; N, 3.67%. Found: C, 78.41%; H, 13.15%; N, 3.85%.

EXAMPLE 3

1,4-Dioxa-8-aza-7,7,9,9-tetramethyl-spiro[4.5]decane

Into a solution of 23.4 g. of triacetonamine in 150 ml. of benzene were added 83 g. of ethylene glycol and 30 g. of p-toluenesulfonic acid and the resulting mixture was heated under reflux for 18 hours by means of a water separator.

Then, the reaction mixture was treated in the same manner as shown in the above Example 1 to give the desired product as colorless liquids boiling at 103.5°–104.5°C/3.4 mmHg.

IR (liquid film) $\nu_{C-O-C}$ 1091, 1040 cm$^{-1}$ Analysis for $C_{11}H_{21}NO_2$: Calculated: C, 66.29%; H, 10.62%; N, 7.03%. Found: C, 66.39%, H, 10.74%; N, 6.98%. Molecular weight (Osmometer): Calculated: 119.29 Found: 205.7

EXAMPLE 4

4,4-(o-Phenylenedioxy)-2,2,6,6-tetramethylpiperidine

The substantially same procedure as shown in the above Example 3 was repeated except that catechol was employed instead of the ethylene glycol to give the desired product as colorless liquids boiling at 118°–120°C/3 mmHg.

Upon being allowed to cool, the liquids solidified and recrystallization from aqueous methanol gave white crystals melting at 74° – 75°C.

IR (Nujol mull) $\nu_{C-O-C}$ 1098, 1064 cm$^{-1}$. Out-of-plane deformation absorption of the o-disubstituted benzene ring: 730–800 cm$^{-1}$. Analysis for $C_{15}H_{21}NO_2$: Calculated: C, 72.84%; H, 8.56%; N, 5.66%. Found: C, 72.73%; H, 8.71%; N, 5.90%.

EXAMPLE 5

Into 100 parts of polypropylene ["Noblen JHH-G," trade name, available from Mitsui Toatsu Chemicals Inc., Japan, employed after twice recrystallizations from monochlorobenzene] was incorporated 0.25 part of each of the test compounds of this invention indicated below. the resulting mixture was mixed and melted and then molded into a sheet having a thickness of 0.5 mm. under heating and pressure.

As a control for comparative purpose, the polypropylene sheet was prepared in a similar manner to that described above without any of stabilizers.

Then, all of these sheets thus formed were tested for the brittleness time (which means the time, expressed in terms of hour, until the test sheet becomes brittle) under ultraviolet ray irradiation at a temperature of 45°C by means of the fade meter prescribed in Japanese Industrial Standard JIS-1044 entitled "Testing Method of Color Fastness to Light of Dyed Textiles and Dyestuffs," Paragraph 3.8 (in English).

The results are given in the following Table 1.

Table 1.

| Test compound No. | Brittleness time (hours) |
|---|---|
| 2 | 620 |
| 3 | 860 |
| 4 | 960 |
| 6 | 1000 |
| None | 100 |

EXAMPLE 6

Into 100 parts of high-density polyethylene ["Hi-Zex," trade name, available from Mitsui Toatsu Chemicals Inc., Japan, employed after twice recrystallization from toluol] was incorporated 0.25 part of each of the test compounds of this invention indicated below. The resulting mixture was made into a sheet having a thickness of 0.5 mm. by the same procedure as in the above Example 5.

The sheet thus formed was tested for the brittleness time by the same test method as in the above Example 5. The results are given in the following Table 2.

Table 2

| Test compound No. | Brittleness time (hours) |
|---|---|
| 2 | 1400 |
| 4 | 1580 |
| 6 | 1920 |
| None | 400 |

EXAMPLE 7

Into 100 parts of 6-nylon ["CM 1011," trade name, available from Toray Industries Inc., Japan, containing no stabilizer] was incorporated 0.25 part of each of the test compounds of this invention indicated below. The resulting mixture was heated and melted and then molded into a film having a thickness of about 0.1 mm. under pressure by a conventional compression molding machine. The film thus formed was aged under the following aging condition and thereafter subjected to a tensile test to determine the retentions of tensile strength and elongation by a standard method.

Aging Test
1. Exposure to ultraviolet ray for 300 hours in the fade meter described above at 45°C.
2. Aging at 160°C for 2 hours in a Geer's aging tester prescribed in Japanese Industrial Standard JIS-K-6301 entitled "Physical Testing Methods for Vulcanized Rubber", Paragraph 6.5 (in English).

The results are given in the following Table 3.

Table 3

| Test compound No. | Fade meter (after 300 hours) | | Geer's aging tester (2 hours, 160°C) | |
|---|---|---|---|---|
| | Retention of elongation (%) | Retention of tensile strength (%) | Retention of elongation (%) | Retention of tensile strength (%) |
| 2 | 65 | 53 | 64 | 67 |
| 3 | 71 | 55 | 69 | 68 |
| 4 | 72 | 67 | 68 | 71 |
| 6 | 74 | 67 | 70 | 69 |
| None | 6 | 38 | 7 | 52 |

EXAMPLE 8

Into 100 parts of polyurethane prepared from polycaprolactone ["E-5080," trade name, available from The Nippon Elastollan Industries Ltd., Japan] was incorporated 0.5 part of each of the test compounds of this invention indicated below. The resulting mixture was heated and melted and then molded into a sheet having a thickness of about 0.5 mm. The sheet thus formed was subjected to the exposure to ultraviolet ray for 15 hours in the fademeter as specified in the above Example 5 at 45°C and then tested for the retentions of elongation and tensile strength as in the above Example 7.
The results are given in the following Table 4.

Table 4

| Test compound No. | Retention of elongation (%) | Retention of tensile strength (%) |
| --- | --- | --- |
| 2 | 85 | 92 |
| 4 | 88 | 89 |
| 6 | 95 | 94 |
| None | 75 | 53 |

EXAMPLE 9

Into 100 parts of polyvinyl chloride ["Geon 103 EP," trade name, available from The Japanese Geon Co., Ltd., Japan] were incorporated 1.0 part of lead stearate, 0.5 part of dibasic lead phosphite, 0.5 part of barium stearate, 0.5 part of cadmium stearate and 0.2 part of each of the test compounds of this invention indicated below. The resulting mixture was blended and kneaded for 4 minutes on a kneading roll to form a sheet having a thickness of 0.5 mm. The sheet was tested for the discoloration degree thereof by the aging test method set forth below.

Aging Test

1. Exposure for 600 hours to the sunshine carbon apparatus prescribed in Japanese Industrial Standard JIS Z-0230 entitled "Accelerated Weathering Test of Rust Proofing Oils," Paragraph 2.

2. The sheet was aged for 90 minutes at 170°C in the Geer's aging tester prescribed in the above Example 7. The results are given in the following Table 5.

Table 5

| Test compound No. | Discoloration | |
| --- | --- | --- |
| | Sunshine carbon apparatus (after 600 hours) | Geer's aging tester (after 90 minutes, 170°C) |
| 2 | Pale yellow | Yellow |
| 4 | Pale yellow | Pale yellow |
| 6 | Slightly yellowish | Slightly yellowish |
| None | Dark brown | Black |

From the above results it can be seen that the 4-piperidone ketal derivatives of this invention exhibit a high degree of stabilizing effect on synthetic polymers against deteriorations thereof.

What is claimed is:
1. 4,4-(o-Phenylenedioxy)-2,2,6,6-tetramethyl-piperidine.

* * * * *